US010966756B2

(12) United States Patent
Odon

(10) Patent No.: US 10,966,756 B2
(45) Date of Patent: Apr. 6, 2021

(54) DIAMETER REGULATOR OF A DEVICE USED TO EXTRACT AN ELEMENT THAT IS INSIDE A CAVITY AND METHOD OF USE

(71) Applicant: AIR BAG ONE SARL, Luxembourg (LU)

(72) Inventor: Jorge Ernesto Odon, Buenos Aires (AR)

(73) Assignee: AIR BAG ONE SARL, Charles de Gaulle (LU)

( * ) Notice: Subject to any disclaimer, the term of this patent is extended or adjusted under 35 U.S.C. 154(b) by 172 days.

(21) Appl. No.: 16/072,930

(22) PCT Filed: May 5, 2017

(86) PCT No.: PCT/EP2017/060837
§ 371 (c)(1),
(2) Date: Jul. 26, 2018

(87) PCT Pub. No.: WO2017/191321
PCT Pub. Date: Nov. 9, 2017

(65) Prior Publication Data
US 2019/0029724 A1    Jan. 31, 2019

(30) Foreign Application Priority Data

May 6, 2016    (AR) .............................. 20160101288

(51) Int. Cl.
*A61B 17/44*    (2006.01)
*A61B 17/50*    (2006.01)
(Continued)

(52) U.S. Cl.
CPC ............ *A61B 17/442* (2013.01); *A61B 17/50* (2013.01); *A61B 2017/00367* (2013.01);
(Continued)

(58) Field of Classification Search
CPC .................. A61B 17/442; A61B 17/50; A61B 2017/00367; A61B 2017/00557;
(Continued)

(56) References Cited

U.S. PATENT DOCUMENTS 1,782,814 A    11/1930 Froelich
4,875,482 A    10/1989 Hariri et al.
(Continued)

FOREIGN PATENT DOCUMENTS

AR    062010 A3    8/2008
EP    2 716 243 A1    4/2014
(Continued)

OTHER PUBLICATIONS

Written Opinion of the International Searching Authority of PCT/EP2017/060837 dated Aug. 4, 2017.
(Continued)

*Primary Examiner* — Diane D Yabut
(74) *Attorney, Agent, or Firm* — Sughrue Mion, PLLC

(57) ABSTRACT

A regulator diameter device to extract an element that is inside a cavity, which is introduced together with a flexible sleeve and an applicator, which comprises an adjustment strip of flexible material; and at least of a mean to regulate said diameter, with the adjustment strip open. The means to regulate such strip: a hollow case with a distal end and a proximal end, fixed to one of the traction handles, at least one string passes through this case, in which the distal ends of the at least one string, are fixed to the open ends of the adjustment strip, while the proximal ends of the string are fixed to a pulling system. The method of use of regulator diameter device to extract an element that is inside a cavity comprises the following steps: a. Introduce the combination (regulator device and the applicator) inside the cavity until the applicators' cup makes its first contact with the element
(Continued)

to be extracted; b) go on pushing the combination which will open the distal ends of the applicator tentacles; c) once the mayor area of the element to be extracted is passed a first regulation of the adjustment strip is done, pulling the trigger and blocking it in this new position; d) keep on pushing until the final insertion; e) regulate again the adjustment strip until its final measure, being able to measure the diameter of the element to be extracted, which can be read in the pulling system scale; f) inflate the air chamber if the device has one; g) remove the applicator; h) pull the traction handles to extract the element that is inside the cavity.

12 Claims, 7 Drawing Sheets

(51) Int. Cl.
 *A61B 17/00* (2006.01)
 *A61B 90/00* (2016.01)
(52) U.S. Cl.
 CPC ........... *A61B 2017/00557* (2013.01); *A61B 2017/445* (2013.01); *A61B 2090/0817* (2016.02)

(58) Field of Classification Search
 CPC ...... A61B 2017/445; A61B 2090/0817; A61B 17/42; A61B 2017/447; A61D 1/08
 See application file for complete search history.

(56) References Cited

U.S. PATENT DOCUMENTS

| 5,559,413 | A | | 9/1996 | Seto |
| 5,910,146 | A | * | 6/1999 | Alexander ........... A61B 17/442 |
| | | | | 606/119 |
| 6,398,790 | B1 | | 6/2002 | Alexander |
| 8,827,951 | B2 | | 9/2014 | Besser et al. |
| 2004/0015175 | A1 | | 1/2004 | Nguyen |
| 2010/0241134 | A1 | | 9/2010 | Odon et al. |
| 2012/0095476 | A1 | | 4/2012 | Porat et al. |

FOREIGN PATENT DOCUMENTS

| WO | 93/17629 A1 | 9/1993 |
| WO | 2016/184992 A1 | 11/2016 |

OTHER PUBLICATIONS

International Search Report of PCT/EP2017/060837 dated Aug. 4, 2017.

* cited by examiner

DIAMETER REGULATOR OF A DEVICE USED TO EXTRACT AN ELEMENT THAT IS INSIDE A CAVITY AND METHOD OF USE

CROSS REFERENCE TO RELATED APPLICATIONS

This application is a National Stage of International Application No. PCT/EP2017/060837 filed May 5, 2017, claiming priority based on Argentinean Patent Application No. 20160101288 filed May 6, 2016.

APPLICATION FIELD

The current invention refers to an external diameter regulator of a device to extract an element that is inside a cavity, more specifically an external diameter regulator of a device to extract an element that is inside a cavity using Odon device.

PRIOR ART

Nowadays there are many devices used to extract elements that are inside a cavity, that change their shape when they are introduced in the cavity.

Forceps are one of these instruments. Forceps is an obstetrical instrument similar to tongs, which help to remove a baby from the outside. Once each part is introduced in the cavity it tighten on the head of the fetus.

U.S. Pat. No. 1,782,814 from Eugene Froehlich of Nov. 30, 1930: states to be an "obstetrical extractor". This extractor is placed covering the fetus' head. It has strings, which are pulled closing the opening in which the fetus' head is introduced.

U.S. Pat. No. 8,827,951 from Besser and others, of Sep. 9, 2014 states to be "an inflatable catheter and its methods of usage". This catheter includes an external and an internal canal, the internal canal moves regarding to the external, and an inflatable balloon with a first portion fixed to the distal tip of the external canal, and a second portion fixed to the portion of the internal canal that stretches beyond the tip of the external canal. The distal tip of the balloon can introduce, like a telescope with movements in proximal way, the internal canal inside the external.

U.S. Pat. No. 4,875,482 from Hariri of Oct. 24, 1987, states to be "a flexible grasping device". This device consists of a net-like structure that is arranged covering the fetus' head and has, in its distal tip, a cylindrical portion around the fetus' head which closes once pulling from a drawstring.

Patents WO 9317629 of Sep. 16, 1993; U.S. Pat. No. 5,559,413 of Jan. 14, 1997; U.S. Pat. No. 5,910,146 of Jun. 8, 1999 and U.S. Pat. No. 6,398,790 of Jun. 4, 2002, all from Gary Alexander, state to be "a device for assisting during childbirth". This device consists of a hollow, stretched and flexible member that fits around the fetus' head. A drawstring is arranged at the end of the fetus' head, to restrict the opening of this once pulling from the end. To pull the drawstring, the auxiliary element to introduce the device inside the cavity has to be placed.

Argentinean patent application 20070103245, published as AR 062010 A3 of Oct. 8, 2008, states to be a "device to extract elements which are inside a cavity". This device comprises a folded sleeve with an air chamber in said fold, which is disposed around the fetus' head. Once the air chamber is inflated, it is disposed around the fetus' head shackling it.

Patent application US 20040015175 from Nguygen of Jan. 22, 2004 states to be a "tube of air bag design on glove, forceps and vacuum use to open the birth canal during labor delivery". This device comprises a double wrapping glove that leaves at least the first pharynx of the fingers uncovered. The hand with the glove is introduced into the vagina and it inflates. With the uncovered fingers, the baby is grabbed.

All precedent applications showed relatively small device head contact areas, whether because they are like lineal circuits or defined like the one from Nguyen. In Argentine application 20070103245 there is a bigger contact area, however it is still not the originally desired size.

None of the precedent disclose or suggest a reduction or shrinkage of the wide external portion of the device diameter to extract an element that is inside a cavity; and that the tension while reducing the said wide external portion of the diameter is performed on one of the handles and not on the device distal that is in contact with the element to be extracted.

SUMMARY OF THE INVENTION

The invention consists of a flexible sleeve folded in its central area defining the inner and the external sleeve. The free ends of the sleeve are partially connected, and have their corresponding traction handles. The external sleeve has the means to hold the adjustment strip. The external sleeve has, in the inner part, diverse pockets to put the tentacles of an applicator. In one realization, there is also an air chamber, with toroid shape, at least partially fixed to the inner part of the external sleeve, and near the central part of the sleeves with the means to inflate/deflate said air chamber.

The diameter regulator of the device to extract elements which are inside a cavity comprises an adjustment strip, with an average diameter, and at least one mean to modify said diameter, in which the adjustment strip is arrange loosely in the inner part of the external sleeve. Triggering the at least one mean to modify said average diameter, a soft arrangement of the diameter is produced on the element to be extracted in the cavity avoiding an increase in external diameter of the device. The adjustment strip, which presents at least one longitudinal opening, has a circular shape, like a truncated cone or a truncated cone with a circular portion in the side of greater diameter. The mean to modify said average diameter comprises at least: one string and a hollow case with a distal end near the fold, and a proximal end that is fixed to the base of the traction handle of the flexible sleeve.

OBJECTS OF THE INVENTION

It is an object of the present invention to provide a diameter regulator of a device used to extract an element that is inside a cavity in which the diameter of the device is changed to the opposite side of the greater part of the element to be extracted.

Another object of the present invention is to provide regulator of a device used to extract an element that is inside a cavity surrounding an external air chamber that prevents to increase its diameter once it is inflated.

Another object of present invention is to provide a diameter regulator of a device used to extract an element that is inside a cavity that presents less friction during the extraction process to the cavity while reducing the diameter of the device.

Another object of present invention is to provide a diameter regulator of a device used to extract an element that is inside a cavity generating more contact with said element having fewer changes of loosen it. There is better effectiveness in the traction with less air pressure in the fastening of the element to be extracted. By reducing the diameter with an adjustment strip, the device has a more extensive area of support with the element to be extracted.

Another object of present invention is to provide a diameter regulator of a device used to extract an element that is inside a cavity that simplifies the introduction of the device in the cavity, closing the ends of the applicator tentacles while it is being introduced.

Another object of present invention is to provide a diameter regulator of a device used to extract an element that is inside a cavity that reduces the traction force required to extract the element while having a smallest diameter due to the adjustment of the adjustment strip, resulting in a smallest contact between the device and the cavity.

Another object of present invention is to provide a diameter regulator of a device used to extract an element that is inside a cavity that indicates the measurement of the diameter of the element to be extracted.

Another object of present invention is to provide a diameter regulator of a device used to extract an element that is inside a cavity in which it is no necessary to deflate the air chamber to facilitate the displacement of the device in the cavity.

Another object of present invention is to provide a diameter regulator of a device used to extract an element that is inside a cavity in which it can be measured the traction force to which the adjustment strip is submitted.

DETAILED DESCRIPTION OF THE INVENTION

Figure 1:
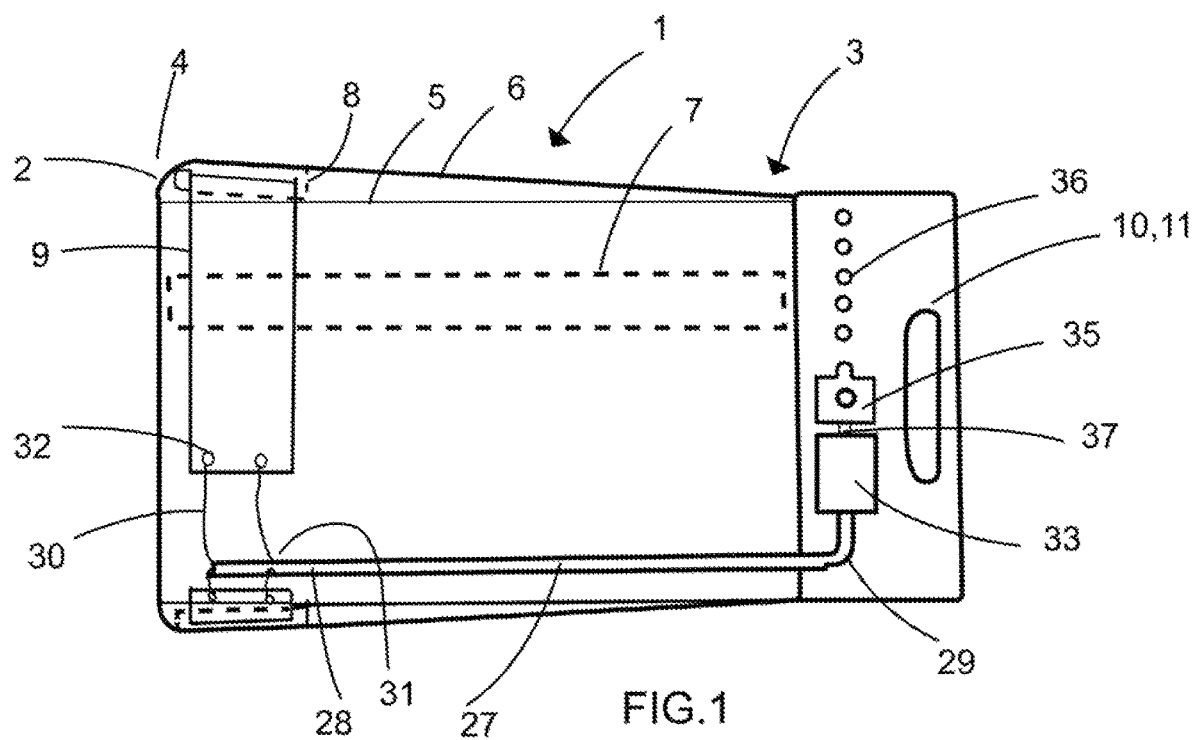
FIG. 1 is a perspective view of a device to extract elements present inside a cavity, without air chamber with the circle shaped regulator diameter installed and in a loosen position.
Figure 2:
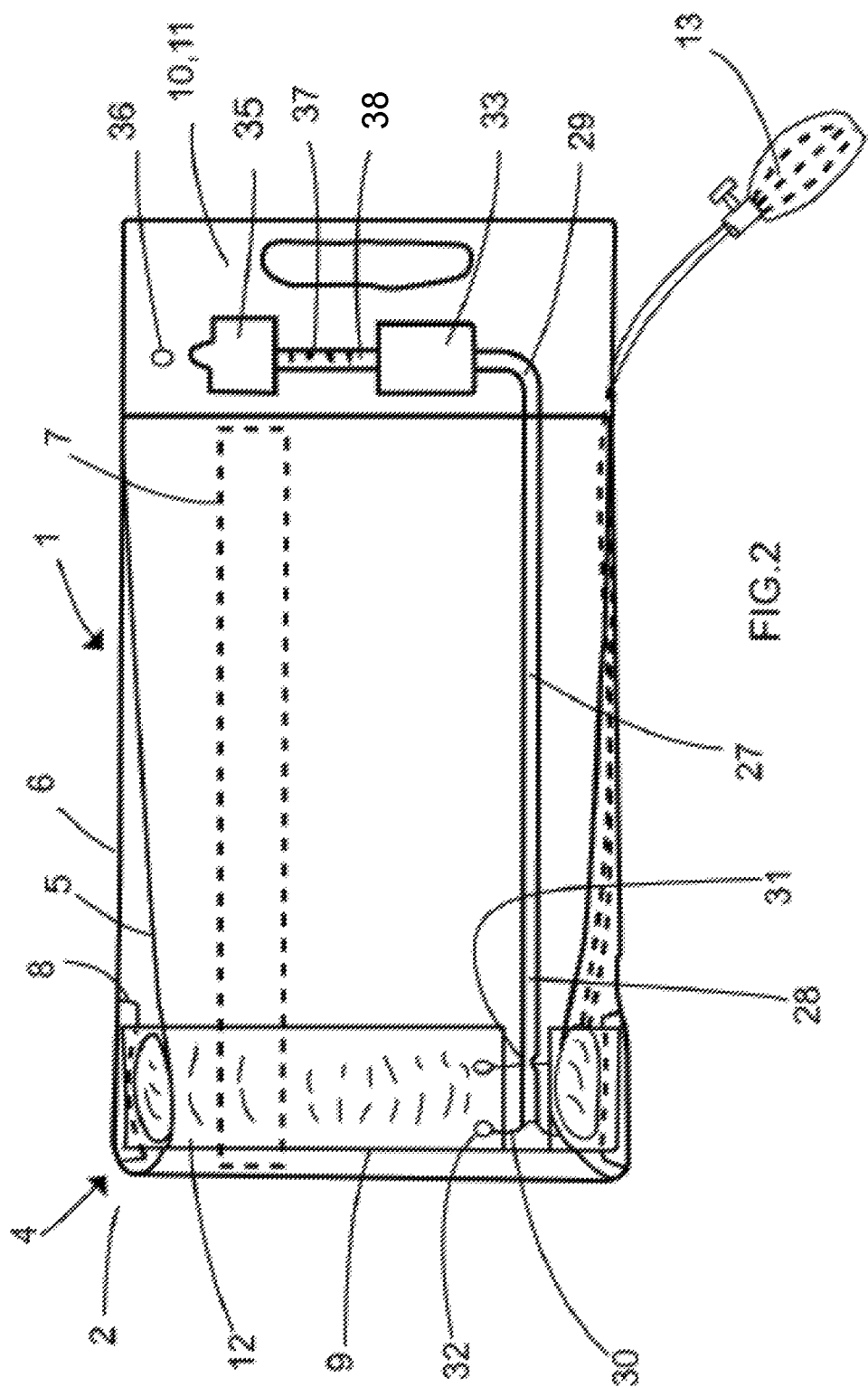
FIG. 2 is a perspective view of a device to extract elements present inside a cavity, with an air chamber with the circle shaped regulator diameter installed, and in regulation position.
Figure 3:
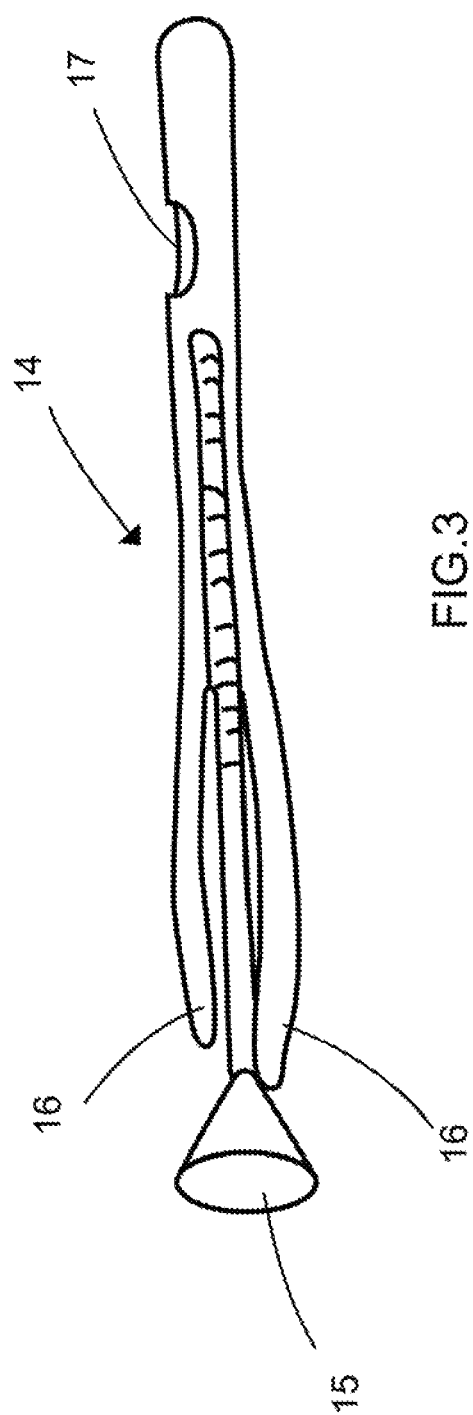
FIG. 3 is a view of an applicator for an element extraction device which are inside a cavity.
Figure 4:
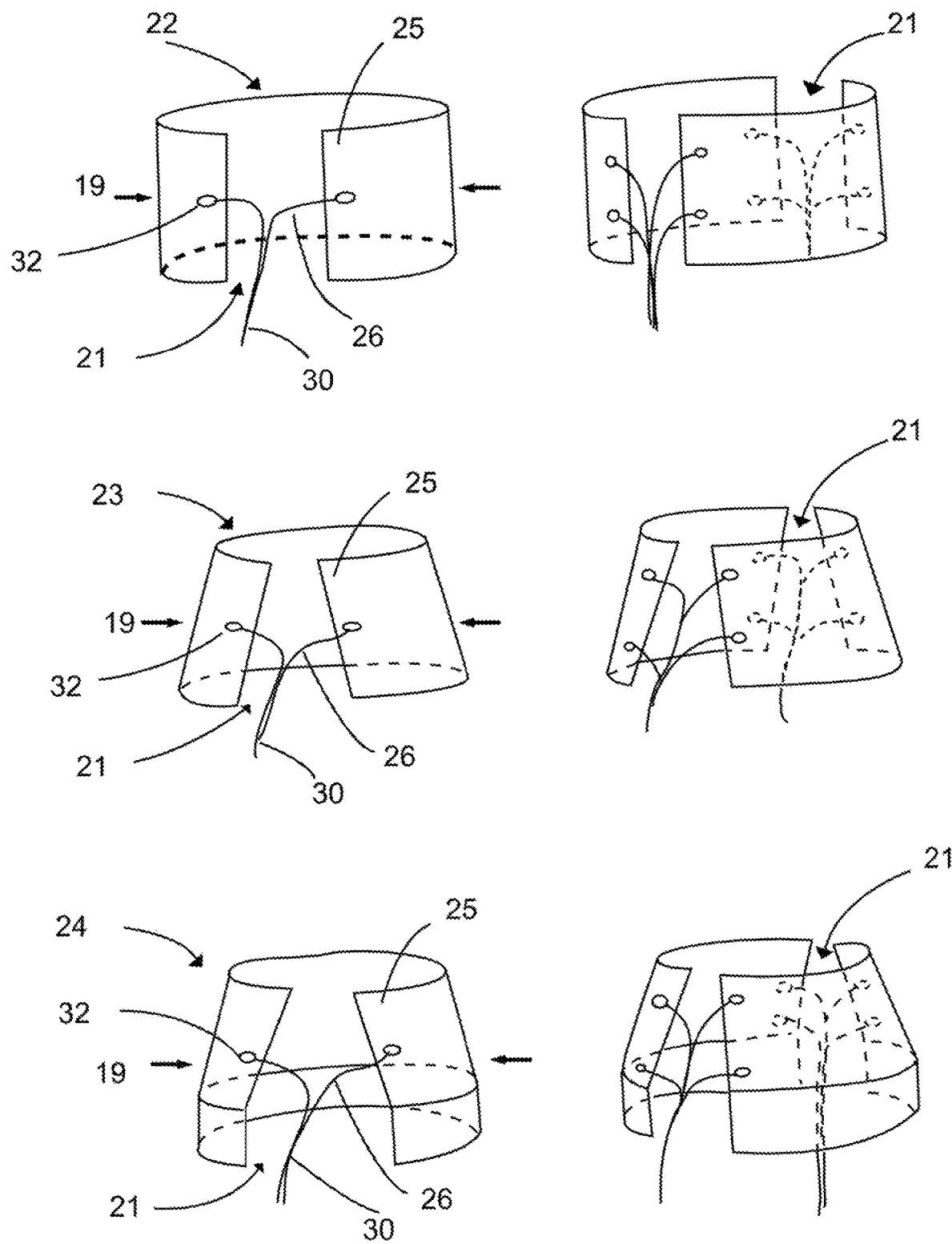
FIG. 4 is a view of perspectives of diverse realizations of adjustments strips.

The diameter regulator of a device used to extract an element that is inside a cavity of the present invention is used together with two known instruments in the states of art:

A flexible folded sleeve (1), with a distal end (2) ready to fit around the element to be extracted, and another proximal end (3) with traction handles, both ends open, presenting in the distal end of the fold (4) which has, an inner sleeve (5) and an external sleeve (6), whose proximal ends are partially connected with each other. The external sleeve has pockets all along (7) and in its inner part to lodge spatulas of the applicator. Also, in the inner part it has the media (8) to hold the adjustment strip (9). These media are on the external side respect to the longitudinal pockets to close the opening of the applicators' tentacles during the introduction process of the device inside the cavity. The proximal end of the flexible folded sleeve has at least two traction handles (10,11) one on each side of the open end, where the base of one of the handles is fixed to the proximal end of the hollow case through which a string passes to regulate the diameter of the device; and in one realization of the flexible sleeve it has an air chamber (12), with teroid shape, fixed to the external sleeve, near the proximity of the fold, so that said air chamber remains between the internal sleeve and the external sleeve. In this case, the fixation of the adjustment strip is performed over the inner part of the external sleeve, so that it can regulate itself on the external diameter of the air chamber. The air chamber has it corresponding means to inflate/deflate (13). An applicator (14) to introduce a flexible folded sleeve inside the cavity that lodges the element to be extracted. The applicator presents a cup (15), spatulas (16) that fit in the longitudinal pockets of the external sleeve and a guide indicator (17) of the movement of the spatulas respect to the cup.

Diameter Regulator of a Device used to Extract an Element that is Inside a Cavity The diameter regulator (18) of a device to extract an element that is inside a cavity, which acts changing the diameter of a flexible sleeve around the element to be extracted or the external diameter of an air chamber, comprises an adjustment strip (9) which has an average diameter (19) when is arranged inside the device, and at least one means to modify the said medium diameter (20).

The adjustment strip, has a width that ranges preferably distal medium of the element to be extracted up to a mayor transversal dimension zone, and with at least one longitudinal opening (21), it has circumference shape (22), of truncated cone (23) or of truncated cone with a circular portion (24) in the widest diameter of the cone. It is placed inside the media to hold said adjustment strip. This means are closed in their transversal sides and open on its longitudinal sides thought which the adjustment strip passes.

When the device is used to assist childbirth, the adjustment strip, preferably has a width that ranges from the shoulders of the fetus up to the high of nose and ears.

In another method, one of the close sides can be opened with a fix mechanism that locks it when the device is being used.

In another method the adjustment strip is formed of diverse separate ribbons, having each of them in their ends the corresponding media to modify the diameter.

In another method, one of the diverse separate ribbons is linked within itself, not with the need a media to modify the diameter, but with a system of fastening/unfastening. The fastening system can be with Velcro closure or with a clasp. This will be useful to put the adjustment strip around the sleeve and inside the media to hold the adjustment strip.

The adjustment strip and the media to modify the diameter are made of a flexible material.

On each end (25) of the adjustment strip (9) a distal end is fixed (26) of at least one string. The link between the adjustment strip and the at least one string is such that, by pulling the opposite end of said string, the regulation strip modifies the diameter and that of the device according to the necessity, having an extraction device of elements content in a cavity with diverse external diameters.

The way to regulate the diameter of the adjustment strip is triggered through a pulling system of a string or something similar.

The configuration between the inner sleeve and the element to be extracted is fundamental for its correct extraction. A combination of the contact area and the diameter of the inner sleeve will generate that the element to be extracted shall remain perfectly inside the device in a way that, by pulling the handles in the open end of the sleeves, it is dragged along the cavity until it appears through it. A width area of contact will make less pressure directly on the element to be extracted.

When it is used to assist childbirths, the configuration of the contact between the sleeve and the cephalic pole of this invention is substantially of higher quality than in other devices of previous art. With forceps the contact area is of two rectangles that face each other slightly curved under the lower jaw. In those devices that used a circular net, the contact area, which is closed with a rope under the chin of the fetus, includes the mouth, the nose, the ears and the eyes and reach almost the fontanel. The head of the fetus is submitted to pressure while pulling from the device. This pressure in the cephalic pole is produced by the deformation of the net of square spaces to rhomboidal spaces. Being the longitudinal axis stretched the transversal axis is reduced, causing the net to reduce over the cephalic pole. This extensive contact area is not what is pretended to be achieved, but the one that is the result of the design of the own circular net, in the case of the inflatable glove, the contact areas correspond to the tip of the fingers.

In this realization, being a strip of considerable width and able to regulator anatomically around the cephalic pole, the result is a contact area that only includes the high of the nose or ears. It is never around the neck only, because due to the width of the adjustment strip, even though the device of extraction is supposed on the shoulders of the fetus, there will always be a portion of said adjustment strip that will concur with the jaw, chin and the nape of the fetus. The design of the adjustment strip will determine the size and the location of the contact area while pulling the device. The same shall happen in case the adjustment strip acts only over the external diameter of the air chamber. The combination of the pressure from the air chamber and the adjustment strip shall make the internal diameter of the air chamber to make pressure over the cephalic pole assuming its morphology. With the regulation of the adjustment strip a widest contact area shall be possible and with lesser pressure while inflate it.

In another embodiment, one of the ends of the adjustment strips is directly fixed to the hollow case, regulating the diameter of the adjustment strip only with one side of said strip.

Sleeve

A sleeve, of flexible material, that presents a folding in its central area, and in the proximity of said fold means to support the adjustment strip in a loose way. Said means area preferably open supports of transversal orientation in respect to the sleeves in which said adjustment strip is arranged. These means are on the inner side of the external sleeve.

Pulling System

Figure 5:
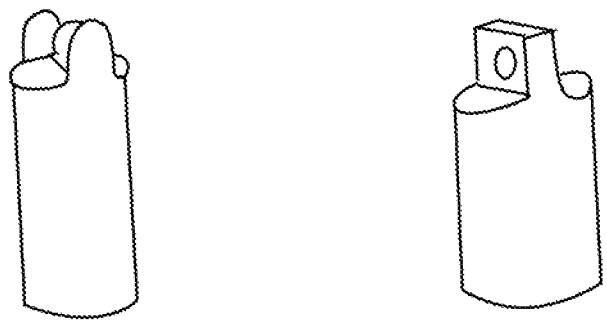
FIG. 5 is a view of perspective of different realizations of the distal end of the hollow case.
Figure 6:
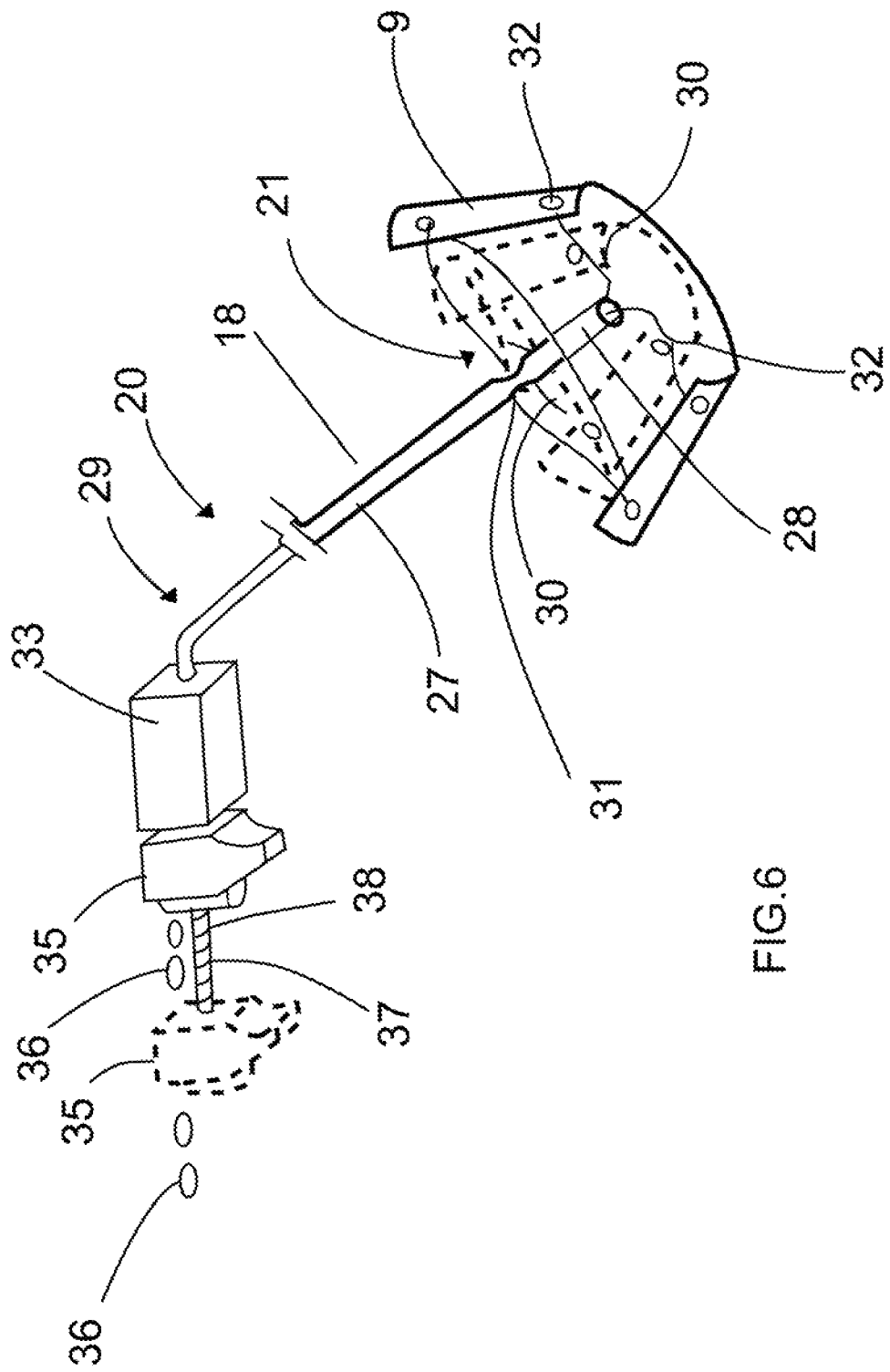
FIG. 6 is a view of a diameter regulator with its components with the proximal end of the hollow case fixed to the traction handle with the pulled mechanism, showing with a solid line the regulator in loosen position and with a line of dots the regulator in fixed position.
Figure 7:
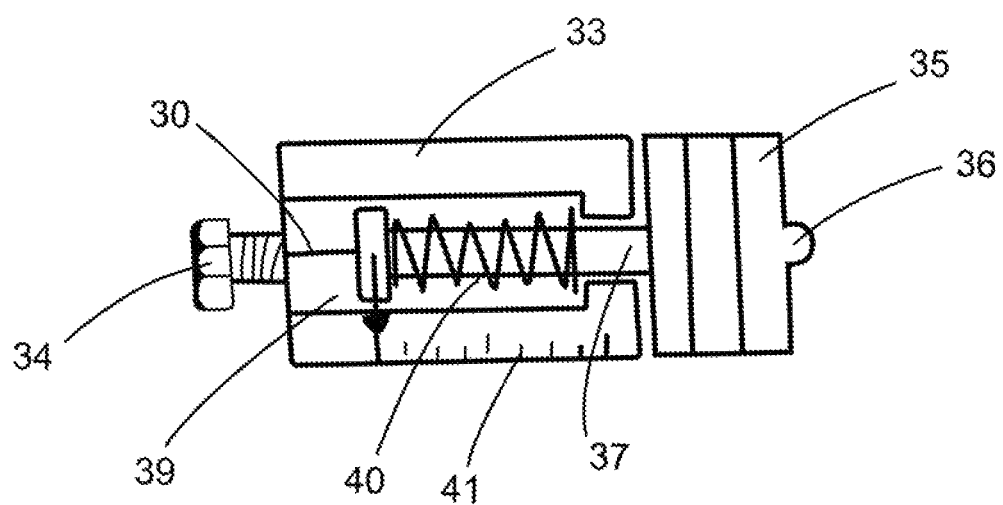
FIG. 7 is a view of a preferred realization of a case support.

The pulling system comprises a hollow case (27) located between two sleeves, with the distal end (28) near to the folding area and the proximal end (29) on the handles side, being this end fixed to one of the handles. The string or similar element (30) is introduced inside a hollow case through the distal end or through a lateral hold (31) near to said end and goes over inside the hollow case, so that one of its ends fix to the adjustment strip in the attachment points (32) located in the open end of the adjustment strip. In case there is more than one strip, the separation between the attachment points of the adjustment strip can have, or not, the same separation among the entrances of the string to the hollow case. To make the pulling operation easier, the distal end of the hollow case can be put in a way that allows the strings to enter in parallel way to the hollow case. FIG. 5 depicts the disposition of a hub and of a buttonhole.

In a preferred realization, the proximal end of the hollow case is linked to a case support (33) fixed to one of the traction handles through a hollow tension screw (34). This hollow tension screw will be used to adjust the tension of the hollow case. The support of the case has a hole collinear with the access to the case and a guide over which the pulling trigger (35) slides. The at least one of the strings that passes through the hollow case, the tension screw and the collinear hole of support of the case, fix to an axis (37) that is fixed to the pulled trigger. This axis inside the collinear hole of support of the case between two extreme positions. In the position when the adjustment strip is release, the axis is introduced into the support of the case and in the position of when the adjustment strip has reduced the diameter of the device, the axis is moved and the trigger blocked in holes (36) of one of the handles. The axis can present a graduated scale (38) that shows the measurement of the diameter that is being hold In another method, the adjustment strip can be parted in more than one place, being for this reason, formed by at least two sections of the adjustment strip. Each pair of ends of the strip hall have its corresponding pulling media.

In another method, the pulling system has a dynamometer (39) connected to the at least one strip that shows the tension to which it is submitted said string and, at the same time, shows the tension to which the adjustment strip is submitted. By putting traction on the device to extract the element, the adjustment strip, already regulated, shall pressure over the element to be extracted to drag it, together with the device, outside the cavity. In case of any action from the element to be extracted of remaining in its position respect to the cavity, the regulation strip shall undergo a traction that will be seen in the tension of at least one string. Once the traction of the device increases, and being the element to be extracted opposing to this traction, the higher will be the tension that the at least one string, the adjustment strip and the element to be extracted suffer. This tension can be important because it can generate undesirable effects on the element to be extracted. By placing coaxially a dynamometer with the at least one string the values of the tension can be controlled. The dynamometer can be a spring (40) or a scaled spring (41).

When used for assisting during childbirth, the tension of the force shall be limited not to damage the cephalic pole.

Method of Use

The device already to be used presents a flexible folded sleeve, with the adjustment strip in the position inside the medias to hold the device, and the end of the hollow case fixed to one of the traction handles. The adjustment strip is arranged loose. The extraction device is assembled introducing the applicator tentacles inside the pockets of the sleeve, forming a combination of the device with the regulator and the applicator. This is introduced inside the cavity until the tip of the applicator makes a first contact with the element to be extracted. The pushing of the combination continues and this generates the opening of the distal ends of the applicator. Once the greater area of the element to be extracted is passed, a first regulation of the adjustment strip is done. Pulling the trigger and blocking it in its new position, in this first regulation, the angles of the ends of the tentacles will be modify falling back on the element to be extracted. The cavity axis cause them to be parallel, and what is more, it will shorten the external diameter of the device, reducing the pressure over the walls of the cavity. The distal ends of the tentacles shall make no pressure against the wall of the cavity due to keep on pushing; this way, the pressure against the walls of the cavity shall be reduced. The pushing continues until the insertion is over. In the final position of the combination, the adjustment strip is regulated one more time up to its final measure, letting the measure of the diameter of the element to be extracted to be measured, which is seen in the pulling system. If the sleeve has an air chamber, it can be inflated, and the external diameter shall not be increase due to the restriction that the regulated adjustment strip imposes. The applicator is removed. It is pulled from the traction handle to remove the element that is inside the cavity, having the possibility to increase the inflation pressure if it were necessary.

In case of use for assisting during childbirth, when the device has an air chamber, little before the crowning, the chamber has to be deflate, because there is no enough room for the cephalic pole, the bag and the inflated air chamber. The deflate has to be done in a precise moment, because it is performed beforehand the cephalic pole can be loosen extracting the device without the fetus, and it is performed with delay it can produce tears in the birth canal. With the present invention, it is not necessary to have an air chamber because the adjustment strip with trunk shape of cone drags easily the cephalic pole.

This realization, not disclose or suggested in any of the prior art to extract an element that is inside the cavity, consists of the following steps:

Introduce the combination (the device with regulator and the applicator) inside the cavity until the tip of the applicator makes its first contact with the element to be extracted. Continue pushing the combination that will began to open the distal ends of the applicator tentacles; once an the largest section was passed the element to be extracted makes a first regulation of the adjustment strip, pulling the trigger and blocking it in a new position. Keep on pushing until the insertion is completed. Regulate again the adjustment strip up to its final measure, being able to measure the diameter of the element to be extracted, inflate the air chamber, if the device has one. Remove the applicator and pull the traction handles to extract the element that is inside the cavity. If the regulator has a dynamometer, the operator of the device may be able to see at all times the transversal tension that is being execute over the element that has to be extracted. When it reaches a certain limit, the traction of the device may be reduce to decrease the tension of the adjustment strip.

The invention claimed is:

1. A regulator diameter device to extract an element that is inside a cavity, comprising:
    a flexible folded sleeve;
    an applicator;
    wherein the flexible folded sleeve has both ends open with a fold in a distal end of the flexible folded sleeve, the flexible folded sleeve has an inner sleeve and an external sleeve, with proximal ends of the inner sleeve and the external sleeve at least partially linked, and a proximal end of the flexible folded sleeve has at least two traction handles, and pockets to lodge spatulas of the applicator, and
    wherein the applicator has a cup, spatulas that fit in the pockets of the flexible folded sleeve and an indicator guide for movement of the spatulas with respect to the cup,
    and wherein
    the regulator diameter device further comprises an adjustment strip of flexible material secured at or near the distal end of the flexible folded sleeve and having a circumferential shape with a longitudinal cut; and
    means for modifying a diameter of the adjustment strip, the means modifying fixed to edges of the longitudinal cut.

2. The regulator diameter device to extract an element that is inside a cavity of claim 1, wherein the adjustment strip forms a cone shape or a truncated cone shape with a circular portion in a widest diameter part of the adjustment strip.

3. The regulator diameter device to extract an element that is inside a cavity of claim 1, wherein the adjustment strip is fixed loosely to the inner sleeve through an opening and oriented transverse to a longitudinal direction of the inner sleeve orientation to hold it.

4. The regulator diameter device to extract an element that is inside a cavity of claim 1, wherein the means for modifying comprises a pulling system for triggering the means for modifying and that comprises:
    a hollow case with a distal end on or proximate the fold of the flexible folded sleeve and a proximal end fixed to one of the two traction handles,
    at least one string or similar element, which is introduced inside said hollow case such that distal ends of the at least one string or similar element are fixed to open ends of the adjustment strip at attachment points, while proximal ends of the at least one string or similar element are fixed to the pulling system.

5. The regulator diameter device to extract an element that is inside a cavity of claim 4, wherein the at least one string or similar element is guided into the hollow case by a medium such that the at least one string or similar element is aligned parallel to the hollow case.

6. The regulator diameter device to extract an element that is inside a cavity of claim 5, wherein said medium is a guide hole.

7. The regulator diameter device to extract an element that is inside a cavity of claim 4, wherein:
    the proximal end of the hollow case is linked to a fixed support of the hollow case fixed to one of the traction handles by a tension screw the fixed support having a hole collinear with an access hole of the hollow case and a guide over which a trigger of the pulling system slides with means for blocking the trigger; and
    the at least one string or similar element that passes through the hollow case, the tension screw and the collinear hole is fixed to a fixed axis of the pulling system.

8. The regulator diameter device to extract an element that is inside a cavity of claim 7, further comprising a graduated scale along the fixed axis to show the changes in the diameter of the adjustment strip.

9. The regulator diameter device to extract an element that is inside a cavity of claim 4, wherein the at least one string or similar element is connected with a scaled dynamometer that shows a tension of the at least one string or similar element.

10. The regulator diameter device to extract an element that is inside a cavity of claim 1, wherein the means for modifying a diameter of the adjustment strip comprises an elongated strip of material attached to the adjustment strip at or near the longitudinal cut and intermediate to proximal and distal ends of the adjustment strip relative to a longitudinal axis of the regulator diameter device; and wherein pulling of the elongated strip of material causes a reduction in the diameter of the adjustment strip about the longitudinal axis.

11. The regulator diameter device to extract an element that is inside a cavity of claim 1, wherein the adjustment strip has a cone shape such that, when used to extract a fetus, is configured to extend anatomically around a cephalic pole so as to have a contact area that includes at least a portion of a nose or ears.

12. A method of using the regulator diameter device to extract an element that is inside a cavity of claim 1, comprising the following steps:

a) inserting the regulator diameter device, including the applicator inside the cavity until the cup contacts the element to be extracted;

b) further inserting of the regulator diameter device to thereby cause distal ends of the applicator to spread apart;

c) once a major area of the element to be extracted is passed, a first regulation of the adjustment strip is done, by actuating a pulling system and blocking the pulling system in a new position;

d) continuing to insert the regulator diameter device until a final insertion point;

e) regulating again the adjustment strip to a final diameter and measuring a corresponding diameter of the element to be extracted, when the pulling system has a diameter measurement scale;

f) inflating an air chamber when the device has an air chamber;

g) removing the applicator;

h) pulling the traction handles to extract the element that is inside the cavity.

\* \* \* \* \*